United States Patent
Yamamoto et al.

(10) Patent No.: US 6,610,515 B1
(45) Date of Patent: Aug. 26, 2003

(54) FELINE GRANULOCYTE COLONY-STIMULATING FACTOR

(75) Inventors: Akira Yamamoto, Tokyo (JP); Kotaro Tuchiya, Tokyo (JP); Akira Iwata, Tokyo (JP); Susumu Ueda, Saitama (JP)

(73) Assignee: Nippon Institute for Biological Science, Tokyo (JP)

( * ) Notice: Subject to any disclaimer, the term of this patent is extended or adjusted under 35 U.S.C. 154(b) by 0 days.

(21) Appl. No.: 09/530,095

(22) PCT Filed: Oct. 23, 1998

(86) PCT No.: PCT/JP98/04809

§ 371 (c)(1), (2), (4) Date: Apr. 24, 2000

(87) PCT Pub. No.: WO99/20652

PCT Pub. Date: Apr. 29, 1999

(30) Foreign Application Priority Data

Oct. 23, 1997 (JP) ................................................. 9-291055

(51) Int. Cl.[7] .......................... C12N 5/10; C12N 15/27; C12N 15/63; C07K 14/53; A61K 38/19

(52) U.S. Cl. ...................... 435/69.5; 536/23.5; 530/351; 424/85.1; 435/71.1; 435/71.2; 435/471; 435/320.1; 435/325; 435/252.3; 435/254.11

(58) Field of Search ............................... 536/23.1, 23.5; 530/351; 424/85.1; 435/69.5, 71.1, 71.2, 471, 320.1, 325, 252.3, 254.11

(56) References Cited

U.S. PATENT DOCUMENTS 5,606,024 A    2/1997    Boone et al.

FOREIGN PATENT DOCUMENTS

| JP | 7-102151 | 11/1995 |
|---|---|---|
| JP | 2527365 | 8/1996 |
| JP | 2660178 | 12/1997 |

OTHER PUBLICATIONS

Nomura et al., "Purification and Characterization of Human Granulocyte Colony–Stimulating Factor (G–CSF)," *The EMBO Journal*, vol. 5, No. 5, pp. 871–876 (1986).

Nagata et al., "The Chromosomal Gene Structure and Two mRNAs for Human Granulocyte Colony–Stimulating Factor," *The EMBO Journal*, vol. 5, No. 3, pp. 575–581 (1986).

Lothrop et al., "Correction of Canine Cyclic Hematopoiesis With Recombinant Human Granulocyte Colony–Stimulating Factor," *Blood*, vol. 72, No. 4, pp. 1324–1328 (1988).

Hammond et al., "Chronic Neutropenia: A New Canine Model Induced By Human Granulocyte Colony–Stimulating Factor," *J. Clin. Invest.*, vol. 87, pp. 704–710 (1991).

Smith et al., "Production of Human Beta Interferon in Insect Cells Infected with a Baculovirus Expression Vector," *Mol. Cell. Biol.*, vol. 3, No. 12, pp. 2156–2165 (1983).

Howard et al., "Identification of a T Cell–Derived B Cell Growth Factor Distinct From Interleukin 2," *J. Exp. Med.*, vol. 155, pp. 914–923 (1982) and.

Conlon et al., "Murine Thymocytes Proliferate in Direct Response to Interleukin–7," *Blood*, vol. 74, No. 4, pp. 1368–1373 (1989).

*Primary Examiner*—Prema Mertz
(74) *Attorney, Agent, or Firm*—Reed Smith LLP

(57) ABSTRACT

The present invention provides a medicine which promotes the production of neutrophiles in case the number of the neutrophiles decreases upon treating the tumor of a cat, and does not have side-effects, wherein said medicine is prepared by incorporating, as an active ingredient, a protein which consists of 174 amino acids, and has an activity as a feline granulocyte colony stimulating factor.

6 Claims, 1 Drawing Sheet

FIG. 1

```
Human   MAGPATQSPMKLMALQLLLWHSALWTVQEATPL-*---GPAS-SLP     40
Mouse   ··QLSA·RR············Q····SGR··V··VTVSAL·P·LP··    46
Cat     ···T········H····MVQ···········------··T-···        31

QSFLLKCLEQVRKIQGDGAALQEKLVSECATYKLCHPEELVLLGHS      86
        R·····S·········AS·SV·L·E---·················      89
        ·············V·A··T··Q·R-----··AH·············A    74

LGIPWAPLSSCPSQALQLAGCLSQLHSGLFLYQGLLQALEGISPEL     132
        ····K·S··G·S·····QTQ·········C·········S····A·     135
        ····Q······S······T··R·················A······    120

GPTLDTLQLDVADFATTIWQQMEELGMAPALQPTQGAMPAFASAFQ     178
        A····L······N···········N··V··TV····S····T····    181
        A····M····IT···IN······DV·····VP····T··T·T····    166

RRAGGVLVASHLQSFLEVSYRVLRHLAQP                      207
        ·······AI·Y··G···TARLA·H···                        206
        ·····T····N········A··A···FTK·                     195
```

FELINE GRANULOCYTE COLONY-STIMULATING FACTOR

TECHNICAL FIELD

The present invention relates to a feline granulocyte colony stimulating factor and a gene which codes for the factor, and, more particularly, to a feline granulocyte colony stimulating factor which is useful as a substance which functions mainly for the production of neutrophiles and maintenance of its functions in a cat, and to a method for producing the same.

BACKGROUND ART

It is already known that a granulocyte colony stimulating factor (G-CSF) functions mainly for the production and activation of neutrophiles which are essential for the defense in vivo. For example, human G-CSF was, for the first time, purified from "CHU-2" cells by Nomura et al. and its amino acid sequence was determined (Nomura et al., 1986, EMBO J., 5, p.p.871–876).

In addition, Nagata et al. carried out the cloning of its cDNA (Nagata et al., 1986, EMBO J., 5. p.575–581).

Human G-CSFs are secretory proteins which have a molecular weight of about 19 kDa. One of them consists of 204 amino acids, and contains a signal sequence which consists of 30 amino acids. Another consists of 207 amino acids. Val-Ser-Glu is inserted between Leu35 and Cys36 of the former to give the latter. As a result, the in vitro biological activity of the latter G-CSF is about one tenth of the former. It is considered that the former, which consists of 174 amino acids and is more active, mainly exists and plays important roles in vivo.

If a recombinant human G-CSF pharmaceutical preparation is administered in vivo, it stimulates the production of neutrophiles at very high yield and effectively depending on the dose and the period, enhances the number of peripheral blood neutrophiles, activates the function of the increased mature neutrophiles, and mobilize the hematopoietic stem cells to the peripheral blood. These phenomena disappear rapidly after the administration is stopped. In addition, even if a considerably large amount of it is administered, side effects are seldom observed. Even if it is administered for a long period, the stem cells are not exhausted, and antibodies are not produced. Therefore, it can be used for the supporting therapy after chemotherapy for cancer or bone marrow transplantation in order to recover quickly from neutropenia to avoid serious infectious diseases.

Recently, chemotherapy are also used for the treatment of tumors in cats. When neutrophiles decrease as in the case of human, a medicine is necessary which promotes the production of neutrophiles, but which does not have side effects. Therefore, a G-CSF, which is safe and has a strong effect, is required.

The technique to produce a large amount of a feline G-CSF by breeding cats or by culturing cells derived from a cat, has not been established yet. Purification of a feline G-CSF has not been tried, either. Therefore, it was difficult to obtain an enough amount of a feline G-CSF which is necessary for treating cats.

When dogs suffering from periodic neutropenia were treated with a human recombinant G-CSF, leukocytes increased significantly and the neutropenia was on the way to convalescence in a short period, but neutralization antibody against the human G-CSF was produced later on (Lothrop et al., 1988, Blood, 72, p.1324–1328; Hammond et al., 1991, J. Clin. Invest., 87, p.704–710).

Probably a similar phenomenon will occur in cats. It is presumably difficult to use a human or other animal's recombinant G-CSF for treating cats for a long period.

DISCLOSURE OF THE INVENTION

To solve the above-mentioned problems, the inventors cloned a gene encoding a feline G-CSF to supply biologically active feline G-CSF protein inexpensively, and prepared an expression vector which has said gene. Thus the present invention was completed.

The invention according to claim 1 is directed to a protein which has I) amino acid sequence no. 2 (SEQ ID NO. 2) or II) an amino acid sequence which is obtained by deleting, substituting, adding, or inserting one or more amino acid(s) from, in, to, or into amino acid sequence no. 2 (SEQ ID NO. 2), and which has a biological activity as a feline G-CSF. The properties of amino acid sequence no. 2 (SEQ ID NO. 2) are as follows:

Sequence length: 174
Sequence type: amino acid
Topology: linear
Kind of sequence: protein
Source: cat (family Faridae, genus Felis, species catus)
Property of sequence:
  characterizing symbol: feline granuloctye colony stimulating factor
  Position: 1-174
  Method for determining property: P A protein which has amino acid sequence I and a biological activity as a feline G-CSF can be transcribed and translated from a gene fragment which has nucleotide sequence no. 1 (SEQ ID NO. 1) or a genomic gene which codes for a feline G-CSF, or can be produced, for example, by the chemical synthesis. Nucleotide sequence no. 1 (SEQ ID NO. 1) can be obtained by the chemical synthesis, the DNA replication, the reverse transcription, the transcription, and other methods.

A protein which has the above-mentioned amino acid sequence II which is obtained by deleting, substituting, adding, or inserting one or more amino acid(s) from, in, to, or into amino acid sequence no. 2 (SEQ ID NO. 2) and a biological activity as a feline G-CSF is encoded by a gene which is obtained by deleting, substituting, adding or inserting base(s) which correspond(s) to the above-mentioned amino acid(s) from, in, to, or into nucleotide sequence no. 1 (SEQ ID NO. 1). This protein can be transcribed and translated from this gene, or can be synthesized, for example, by a chemical method in a manner which is similar to the above-mentioned case.

According to the present invention of proteins which-have the above-mentioned amino acid sequences, a veterinary pharmaceutical composition which contains, as an active ingredient, a protein which has a biological activity as a feline G-CSF can be provided, and the composition can be effectively used as medicines for neutropenia.

In addition, a specific antibody can be obtained using the feline G-CSF protein by the well known method. This antibody can be used for immunologically detection of a G-CSF in a cat. Therefore, the said antibody can be used as a sensor for detecting and diagnosing the level of a G-CSF in a cat. In addition, the antibody can be used in the affinity chromatography for isolating and purifying said feline G-CSF protein from products by a transformant which is described below.

The present invention provides a host (transformant) which was prepared to produce said protein by recombinant techniques to express for the above-mentioned feline G-CSF gene, and a method for inexpensively producing a feline G-CSF protein using the transformant.

The above-mentioned transformant can be prepared, for example, as a 'feline G-CSF'-producing cell.

In case the host cell is an eukaryotic cell, a 'feline G-CSF'-producing cell can be prepared by linking a DNA fragment which has a feline G-CSF gene fragment which has nucleotide sequence no. 1 (SEQ ID NO. 1) at downstream to a promotor, such as one from viruses, followed by introducing it to eukaryotic cells. In case a recombinant virus vector such as baculovirus is used, a recombinant virus vector can be prepared, for example, according to the method described by Smith et al. (Smith et al., Mol. Cell. Biol., 3, p. 2156–2165). A transfer vector can be constructed by inserting a DNA fragment which codes for a feline G-CSF at downstream of a polyhedrin promotor of a baculovirus. The resultant transfer vector is transfected into an insect cell together with a baculovirus genome DNA. Recombinant virus clones can be selected whether they can produce G-CSF activity when infected to insect cells. In addition, a recombinant baculovirus can be prepared which produces feline G-CSF when infected to the host insects.

In case a host cell is a prokaryotic cell, a 'feline G-CSF'-producing cell can be prepared, for example, by insertion of a DNA fragment which codes for a feline G-CSF protein to an expression vector, followed by transforming the prokaryotic cell.

These recombinant techniques can be carried out according to well-known, generally used protocols. Its expression efficiency can be regulated by the gene manipulation techniques and cell engineering techniques, for example, by the addition or modification of a signal sequence, the selection of a suitable host-vector system, and by the modification of an expression-regulating site of a gene. By selecting a host, the protein can also be obtained which has appropriate sugar chain(s).

The objective feline G-CSF proteins can be obtained by culturing the above-mentioned transformed cell, followed by recovering and purifying the produced proteins.

Purification of proteins from the above-mentioned cultured cells can be carried out by usual methods including the affinity chromatography, preferably the affinity chromatography which has resin conjugated with the above-mentioned specific antibody.

Therefore, by using a transformant described above, prepared according to the present invention, feline G-CSF proteins can be produced in a large amount, and can be used as medicines for neutropenia of cats.

These procedures can be carried out according to well known gene manipulation techniques and cell engineering techniques which were described, for example, by Sambrook et al. (Sambrook et al., 1989, Molecular cloning: a laboratory manual, 2nd edition, Cold Spring Harbor, N.Y.: Cold Spring Harbor Press).

BRIEF DESCRIPTION OF THE DRAWINGS

FIG. 1 illustrates amino acid sequences of human (SEQ ID NO. 28), mouse (SEQ ID NO. 29) and feline (SEQ ID NO. 30) G-CSFs which are deduced from the corresponding genes. They are aligned so that homologies become maximal. Symbols: •, the same amino acid as the amino acid of sequence of the human G-CSF; –, deletion.

BEST MODE FOR CARRYING OUT THE INVENTION

The feline G-CSF protein which has amino acid sequence no. 2 (SEQ ID NO. 2) can be obtained by, for example:

amplifying an objective gene region by the polymerase chain reaction (PCR) using synthetic DNA primers which were prepared based on nucleotide sequences reported for human, mouse, and dog G-CSF and, using genomic DNA extracted from CRFK cells (ATCC strain CCL-94) which are derived from a feline kidney as template;

determining the nucleotide sequence after cloning the DNA into a commercially available vector;

amplifying genomic DNA regions which are adjacent to the region which was cloned by the PCR method using synthetic DNA primers which were prepared based on the determined nucleotide sequence;

determining the nucleotide sequence after inserting the DNA into the above-mentioned vector; and determining the nucleotide sequence of the genomic DNA which contains the cDNA region which codes for a feline G-CSF protein by repeating the above step.

The cloning of cDNA can be carried out by:

stimulating the above-mentioned CRFK cells with lipopolysaccharide (LPS);

extracting cellular RNA;

preparing cDNA which is complementary to the obtained RNA; and amplifying by PCR using the obtained cDNA as template of region coding for G-CSF using primers prepared, based on the nucleotide sequence of the genomic DNA.

Then, a recombinant baculovirus is constructed by insertion of the amplified cDNA for expression. The objective feline G-CSF protein can be expressed by infection of the recombinant baculoviruses to insect cells, then confirmed by the bioassay of the obtained protein.

EXAMPLES

The present invention is described by way of examples in more detail below.

(1) Preparation of Genomic DNA

Feline kidney epithelial cells CRFK (ATCC strain CCL-94) were cultured using a DMEM medium (Nissui Pharmaceutical) supplemented with 10% fetal calf serum (FCS, GibcoBRL). Genomic DNA was prepared as follows: CRFK cells were grown in 26 culture dishes of a diameter of 9 cm. After culture medium was discarded, the cell sheets were rinsed with phosphate buffered saline (PBS), scraped and collected into four 50-ml tubes. To each tube, 10 ml PBS was added to suspend the cells, then each tube was centrifuged at 1,000 rpm for 10 min. After the supernatant was discarded, 15 ml of HMW buffer (10 mM Tris hydrochloride, pH 8.0; 150 mM sodium chloride; 10 mM ethylenediaminetetraacetic acid, pH 8.0; 0.1% sodium lauryl sulfate) and 100 µg/ml Proteinase K were added to the tube, cells were suspended, and incubated at 37° C. overnight for digesting proteins. The mixture was extracted twice with phenol, and once with phenol-chloroform. Aqueous layer was recovered, and twice volumes of ethanol were added, and stood at −20° C. for 2 h after mixed well. After centrifugation in 6,000 rpm for 30 min at 4° C., a pellet was dissolved in 500 µl/tube of distilled water.

(2) Cloning of Genomic DNA Fragment (2-1) Amplification by PCR

Based on the nucleotide sequence of the well-conserved regions among human, mouse, dog G-CSF genes, DNA primers Hind5'-1 and Eco3'-IV were synthesized, which have the following sequences:

Hind5'-1: 5'-cgccaagttcagagcttcctgctcaagt-3' (SEQ ID NO. 3)

Eco3'-IV: 5'-cggattcctgctgccagatgttgat-3' (SEQ ID NO. 4)

Recognition sequences for restriction endonucleases HindIII (5'-1) and EcoRI (3'-IV) were inserted into these primers at 5'-ends as indicated by underlines. 1 μg of DNA which was prepared in (1), Hind5'-1 primer, Eco3'-IV primer (each final concentration, 0.4 μM), deoxynucleotides (each final concentration, 200 μM), commercially available Vent DNA polymerase and buffer for the polymerase (both New England Biolab, 2U) were mixed to give a final volume of 50 μl, paraffin oil was overlaid on the mixture, and 25 cycles of PCR were carried out, wherein each cycle consists of the following steps: 92° C. for 30 sec, 60° C. for 72 sec, and 55° C. for 60 sec. Paraffin oil was removed from the product, and the PCR product was electrophoresed on 1.5% agarose, and the gel was stained with ethidium bromide, and gel slices containing 860 bp band was excised under UV light, and DNA fragment was extracted from gel using GeneClean Kit Version 2 (Bio 101) according to the manufacturer's instruction. The purified DNA fragment was digested with restriction endonucleases EcoRI and HindIII.

(2-2) Cloning of PCR Product

Commercially available pUC 18 vector was digested with EcoRI and HindIII, and ligated to DNA fragments which were obtained in (2-1) using a Ligation kit (TAKARA). Using the reaction product, competent *E. coli* XLI-Blue was transformed. Selection of transformed *E. coli* was carried out on the plates of a diameter of 9 cm containing 1.6% Bact Agar and LB medium, supplemented with ampicillin at 100 μg/ml. 20 μl of 2% 5-bromo-4-chloro-3-indolyl-β-D-galactoside and 20 μl of 100 mM isopropyl-β-thiogalactoside were absorbed into the agar gel before use. The plates were incubated at 37° C. overnight, and white colonies which were formed on the plates were selected at random, and subsequently cultured in 2 ml of LB medium supplemented with 100 μg/ml ampicillin overnight. Plasmid DNA was extracted and purified from the *E. coli* cells using a Qiagen Plasmid Midi kit (Bio101) according to the manufacturer's instruction. Clones were checked whether they have DNA fragment of an objective size after digested with restriction endonucleases EcoRI and HindIII of their Plasmid DNA. (2-3) Determination of nucleotide sequence A clone was cultured overnight in 16 ml of LB medium supplemented with ampicillin at 100 μg/ml. Plasmid DNA was extracted and purified using a Qiagen Plasmid Midi kit (Bio 101) according to the manufacturer's instruction, and used for the determination of the nucleotide sequence. The nucleotide sequence was determined by the dideoxy sequence method using a Cycle Sequencing™ kit on an A373 sequencer (both ABI).

(3) Genomic DNA Cloning of Adjacent Unknown Region (3-1) Amplification by PCR

For cloning adjacent regions to the genomic DNA fragment obtained in (2-2), the following DNA primers kit1, kit2 (for 5' upstream), kit3, and kit4 (for 3' downstream) (a recognition sequence for restriction endonuclease BamHI is underlined) were synthesized based on the nucleotide sequence obtained in (2-3). LA PCR in vitro cloning kit (TAKARA) was used as described below with some modifications.

kit1: 5'-ctccaccacccctctccagc-3' (SEQ ID NO. 5)

kit2: 5'-cgcggatcctgcagcgcagtgccatcagcctgg-3' (SEQ ID NO. 6)

kit3: 5'-ggcctcctgcaggccctggc-3' (SEQ ID NO. 7)

kit4: 5'-cgcggatccgctggacatcaccgactttgctatc-3' (SEQ ID NO. 8)

The modifications were as follows: 1) restriction endonucleases Sau3AI (TAKARA), NlaIII, and Tsp509I (both New England Biolab) which were not described in the manufacturer's instruction were used for cleaving the genome, and 2) the following cassettes were prepared by ourselves which have the sites for the compatible restriction enzymes. In addition, DNA primers, which are complementary to these cassettes, Cassette Primer C1 and Cassette Primer C2, were also prepared by ourselves. The nucleotide sequences of these are as follows:

Sau3A1 cassette

5'-gtacatattgtcgttagaacgcggaattcgactcactataggga-3' (*) (SEQ ID NO. 9)

3'-catgtataacagcaatcttgcgccttaagctgagtgatatccctctag-5' (SEQ ID NO. 10) N1aIII cassette 5'-gtacatattgtcgttagaacgcggaattcgactcactatagggagactg-3' (*) (SEQ ID NO. 11)

3'-catgtataacagcaatcttgcgccttaagctgagtgatatccctct-5' (SEQ ID NO. 12)

Tsp509I cassette

5'-tacatattgtcgttagaacgcggaattcgactcactataggga-3' (*) (SEQ ID NO. 13)

3'-catgtataacagcaatcttgcgccttaagctgagtgatatcccttaa-5' (SEQ ID NO. 14)

Cassette primer C1

5'-gtacatattgtcgttagaacgcgtaatacgactca-3' (SEQ ID NO. 15)

Cassette primer C2

5'-cgttagaacgcggaattcgactcactatagggaga-3' (*) (SEQ ID NO. 16)

The underlines of these cassettes indicate the recognition sequence of each restriction endonuclease. The underlines in the sequences of cassettes and primers which have symbol "*" indicate a newly added recognition sequence for restriction enzyme EcoRI.

A PCR product was excised by the method which was described in (2-1), and digested with restriction endonucleases EcoRI and BamHI.

In addition, for the cloning of the unknown region of 3' downstream, similar steps were repeated again so as to obtain all the nucleotide sequence information of the coding region for G-CSF, deduced from the nucleotide sequence data of human, mouse, and dog. For the cloning, the following DNA primers kit5 and kit6 which has a recognition sequence for restriction endonuclease BamHI in the underlined parts were synthesized and used:

kit5: 5'-tccagcgccgggcaggagg-3' (SEQ ID NO. 17)

kit6: 5'-cgcggatccctgcagagcttcctggagg-3' (SEQ ID NO. 18)

(3-2) Cloning of PCR Product and Determination of Nucleotide Sequence

Commercially available pGEM-3Zf(+) vector was digested with EcoRI and BamHI, and ligated to the PCR product which was obtained in (3-1) using T4-DNA ligase. Transformation and selection of transformed *E. coli* were carried out as described in (2-2), and clones which have an insert of the objective size were obtained. Determination of the nucleotide sequence was carried out by the method described in (2-3), analysing two or three clones.

(4) Preparation of RNA

RNA was prepared from CRFK as in the case of the preparation of genomic DNA. CRFK was cultured in three 25 cm² plastic flasks to confluence, and the medium was replaced for the medium supplemented with LPS (SIGMA) derived from *E. coli* O 111 at a final concentration of 10 μg/ml, and cultured at 37° C. for 24 h. After the culture medium was discarded, the cells were rinsed with PBS, and 1 ml of solution D (4 M guanidinethiocyante, 25 mM sodium citrate (pH 7.0), 0.5% N-lauroylsarcosine, and 0.1 M 2-mercaptoethanol) was added to a flask to lyse the cells. The lysate from three flasks was collected in a 15-ml centrifugation tube, and genomic DNA was cleaved by passing the lysate through an 18-gauge needle four times. To the solution, 300 μl of 2 M sodium acetate (pH 4.0), 3 ml of phenol saturated with diethyl pyrocarbonate (DEPC)-treated distilled water, and 600 μl of chloroform/isoamyl alcohol (49:1) were added serially with gently mixing at each step. The resultant mixture was vigorously mixed for 10 sec, chilled on ice for 30 min, and centrifuged 2500 rpm for 30 min at 4° C. After centrifugation, the aqueous layer was recovered, then 4 ml of isopropanol was added, and mixed, refrigerated at −20° C. for 1 h, and centrifuged 3500 rpm for 30 min at 4° C. After the supernatant was discarded, pellets were dissolved in 300 μl of solution D again, and transferred to a 1.5-ml microtube. Then, 300 μl of isopropanol was added, mixed, refrigerated at −20° C. for 1 h, and centrifuged 15,000 rpm for 30 min at 4° C. to recover RNA. After the supernatant was discarded, the pellet was rinsed with 80% ethanol, dried, and dissolved in 50 μl of DEPC-treated distilled water.

(5) Cloning of cDNA
(5-1) Amplification of cDNA

For the cloning of cDNA, the following DNA primers 5' START (including initiation codon), 3' END (including stop codon), and 3' RT (for reverse transcription) were synthesized, based on nucleotide sequences of genomic DNAs:

5' START: 5'-cgcggatccatgaagctgaccgccctgc-3' (SEQ ID NO. 19)

3' END: 5'-cgcggatccttttcagggcttggtgaag-3' (SEQ ID NO. 20)

3' RT: 5'-aaatacactcgtgagggagg-3' (SEQ ID NO. 21)

To the primers 5' START and 3' END, a recognition sequence for restriction endonuclease BamHI in their 5' ends is added as indicated by the underlines.

The reverse transcription was carried out using 5 μg of the RNA prepared in (4) as a template and SuperScriptII RNAaseH reverse transcriptase (GibcoBRL) as follows: 5 μg of RNA and 10 pmol of 3' RT primer were mixed, and the volume was adjusted to 12 μl with DEPC-treated distilled water, and the mixture was heated at 70° C. for 10 min, and rapidly chilled on ice. Then 1 μl of 10 mM dNTP, 4 μl of the buffer supplied by the manufacturer of the reverse transcriptase, 2 μl of 0. 1 M DTT, and 1 μl of reverse transcriptase (299 U) were added, and heated at 42° C. for 55 min and 70° C. for 15 min for reaction.

Using 1 μl of the reverse transcription product as a template, Ex Taq polymerase (TAKARA, 2.5 U), and primers 5' START and 3' END (each at final concentration of 0.4 μM), 30 cycles of PCR was carried out, wherein one cycle consisted of the following steps: 94° C. for 60 sec, 55° C. for 30 sec, and 72° C. for 90 sec.

The amplification product of about 470 bp was excised by the method described in (2-1), and digested with restriction endonuclease BamHI.

(5-2) Construction of baculovirus transfer vector

Commercially available baculovirus transfer vector pBac-PAK1 (Clontech) was digested with BamHI, treated with phosphatase, and ligated with cDNA obtained in (5-1) using Ligation kit version 2 (TAKARA) according to the manufacturer's instruction. Competent *E. coli* XLI-Blue was transformed in the reaction mixture, and the transformed *E. coli* was selected on LB agar plates supplemented with ampicillin at 100 μg/ml. Clone whose insert was in the right direction to the polyhedrin promotor of the transfer vector was selected by PCR screening using Taq polymerase (Pharmacia). The PCR was carried out as described in (5-1). The primer 3'-III located in the cDNA was synthesized, and used together with a commercially available DNA primer Bac-1 (Clontech) corresponds to the vector side in the same direction to the polyhedrin promotor:

3'-III: 5'-cagctgcagggcctggct-3' (SEQ ID NO. 22)

Two clones which gave the amplification products of about 390 bp were detected as a result of the PCR. The nucleotide sequence was confirmed by the method described in (2-3), and was designated sequence no. 1 (SEQ ID NO. 1).

Properties of nucleotide sequence 1 (SEQ ID NO. 1) are as follows:

Sequence length: 588

Sequence type: nucleic acid

Strandedness: double

Topology: linear

Kind of sequence: cDNA to mRNA

Source:
  Name: cat (family Faridae, genus Felis, species catus)

Properties of sequence:
  Characterizing symbol: CDS
  Position: 1-585
  Method for determining properties: P Properties of sequence:
  Characterizing symbol: sig peptide
  Position: 1-63
  Method for determining properties: S Properties of sequence:
  Characterizing symbol: mat peptide
  Position: 64-585
  Method for determining properties: S Properties of sequence:
  DNA which code for feline granulocyte colony stimulating factor Properties of sequence:
  Symbol which characterizes sequence: variation
  Position: 174/replace="t"
  Method for determining properties: E The amino acid sequence deduced from the nucleotide sequence consists of 195 amino acids, corresponds to the more active form of human G-CSF. It has a shorter signal sequence by 9 amino acids than those of human and mouse. The feline G-CSF has a high homology value (%) with human and mouse G-CSFs as shown in Table 1 below. Therefore, this cDNA was considered to code for the feline G-CSF.

For confirming this, a recombinant baculovirus was obtained for expression using the plasmid constructed here as trasfer vector.

TABLE 1

Comparison of homology between mammalian G-CSFs

| | Nucleotide sequence (%) | | |
|---|---|---|---|
| | Cat | Human | Mouse |
| Cat | | 86.9 | 77.8 |
| Human | 81.0 | | 77.5 |
| Mouse | 70.3 | 75.0 | |
| | Amino acid sequence (%) | | |

Upper and right figures are homology values between nucleotide sequences, and lower and left figures are homology values between amino acid sequences.

(5-3) Nucleotide Sequence of Feline Genomic Gene

To further confirm the nucleotide and amino acid sequence of feline G-CSF of CRFK cells determined as described above, the nucleotide sequence of cat genomic gene was also determined.

A liver was removed from a 10-month-old cat, shredded with surgery scissors, and was suspended in 100 ml of TE (10 mM Trishydrochloride, pH 8.0; 1 mM EDTA) which was supplemented with 0.6% SDS, then Proteinase K was added to give the final concentration of 100 µg/ml. The mixture was incubated with stirring at 37° C. for two days to digest proteins. The mixture was extracted with phenol-chloroform. Aqueous layer was taken out, 10 ml of 3 M sodium acetate (pH 5.2) and 200 ml of ethanol were added, and the obtained mixture was stirred. Precipitated genomic DNA was winded up with a glass rod, and the obtained DNA was rinsed with 70% ethanol, dried in air, and redissolved in 10 ml of sterilized distilled water.

Based on the nucleotide sequence of the G-CSF gene of a feline CRFK cell, DNA primers which have nucleotide sequences of regions which are adjacent to the initiation codon and the stop codon, 5' OUT primer and 3' OUT primer were synthesized:

5' OUT primer:
  5'-ggaattccaggcctccatgg-3' (SEQ ID NO. 23)

3' OUT primer
  5'-ggaattcgataaatacactcgtgaggg-3' (SEQ ID NO. 24)

These primers (each final concentration, 0.4 µM), 1 µg of feline genomic DNA, deoxynucleotide (each final concentration, 200 µM, and commercially available Vent DNA polymerase (New England Biolab, 2U) were mixed, and the volume of the mixture was adjusted to 50 µl with the buffer for the polymerase (New England Biolab, 2U), and 30 cycles of PCR were carried out, wherein each cycle consists of the following steps: 94° C. for 60 sec, 55° C. for 60 sec, and 72° C. for 180 sec. Using 1 µl of the PCR product as a template, the second PCR was carried as follows.

The second PCR was carried out using the product of the first PCR as a template, with respect to three parts (regions 1-3) which correspond to exons which code for the objective protein. Combination of the primers which were used for each region, and conditions for the PCR are summarized in Table 2 below.

TABLE 2

Primers which were used for amplification of the each region, and conditions for the PCR

| | Region 1 | Region 2 | Region 3 |
|---|---|---|---|
| Primer 1 | 5' OUT | 5'-1 | 5'-IV |
| Primer 2 | Kit2 | 3'-4 | 3' RT |
| PCR condition (30 cycles) | 94° C. for 60 sec<br>57° C. for 60 sec<br>70° C. for 120 sec | 94° C. for 60 sec<br>60° C. for 60 sec<br>72° C. for 120 sec | 94° C. for 60 sec<br>59° C. for 60 sec<br>72° C. for 120 sec |

The nucleotide sequence of 5' OUT primer in Table 2 is shown in (5-3); the nucleotide sequence of Kit2 primer in (3-1), and the nucleotide sequence of 3' RT primer in (5-1).

The nucleotide sequences of other primers are as follows:
  5'-1 primer: 5'-cagagcttcctgctcaagt-3' (SEQ ID NO. 25)
  3'-4 primer: 5'-cctgcaggaggccctggta-3' (SEQ ID NO. 26)
  5'-IV primer: 5'-atgggctgcctgcgtcaact-3' (SEQ ID NO. 27)

The product of the second PCR was electrophoresed on 1.5% agarose gel, and the gel was stained with ethidium bromide. The DNA was purified with GeneClean Spin Kit (BIO 101) according to the manufacturer's instruction. The ends of the excised DNA fragment are phosphorylated, and the fragment was inserted into the SmaI site of commercially available pGEN-3Z(+) vector.

This reaction mixture was mixed with competent *E. coli* XLI-Blue for transformation. Clones which grew on an LB plate supplemented with ampicillin at 100 µg/ml were cultured overnight in 5 ml of LB medium containing ampicillin at 100 µg/ml, and their plasmid DNAs were extracted and purified with Qiagen Plasmid Midi kit according to the manufacturer's instruction, digested with restriction endonucleases EcoRI and SalI, and clones which have an insert of objective size were obtained. Among them, two clones which have DNA fragment of region 1 or region 3 and four clones which have DNA fragment of region 2 were selected, and their nucleotide sequence was determined by the method described in (2-3).

Then the obtained sequence was compared with nucleotide sequence no. 1 (SEQ ID NO. 1). Position 174 of nucleotide sequence no. 1 (SEQ ID NO. 1) was cytosine, while the same position of feline genomic DNA was thymidine, although this mutation does not cause substitution of the amino acid.

Thus it was shown that the amino acid sequence which corresponds to nucleotide sequence no. 1 (SEQ ID NO. 1) is the same as the amino acid sequence which corresponds to the feline genomic gene.

(6) Preparation of Recombinant Baculovirus
(6-1) Transfection

An insect cells, Sf21AE cells, were cultured in Grace's medium (Gibco BRL) which was supplemented with 10% fetal bovine serum (FBS), 1% Bacto Tryptose broth (DIFCO), and 50 µg/ml kanamycin.

If recombination occurs between a transfer vector and baculovirus genomic DNA which was cleaved with a certain restriction endonuclease simultaneously transfected to a Sf2 AE cell, a recombinant baculovirus is obtained which has the one incorporated into the transfer vector. 20 ng of baculovirus genomic DNA BacPAK (Clontech) cleaved with restriction endonuclease Bsu36I and 1 µg of the transfer vector obtained in (5-2) were mixed, and diluted to 8 µl with sterile distilled water. The DNA solution and 8 µl of two-fold diluted Lipofectin™ (Gibco BRL) were mixed, and stood at room temperature for 15 min. Sf21AE cells in a 6-well plate at a density of 1×10⁶ cells/well were rinsed with a serum-free medium, and 1 ml of the same medium and the above-mentioned DNA-Lipofectin™ mixture were added. The cells were cultured at 27° C. for 5 h, and 1 ml of a medium supplemented with serum was added, and the cells were further cultured at 27° C.

(6-2) Plaque Cloning

Recombinant viruses were cloned from the viruses appeared in the culture supernatant by the plaque formation. Nuclear polyhedra were formed in the cells after infected with a wild-type (non-recombinant) baculovirus, so that they are distinguishable. Three days after transfection, the culture supernatant was 10,000-fold diluted with the medium, and 200 µl of the diluted suspension was added to each of the wells of a 6-well plate which contained Sf21AE cells at a density of 1×10⁶ cells/well, and the cells were infected for 1 h. The viral suspension was removed, and a medium which contains 1% Sea plaque agarose (FMC BIO Products) at 37° C. was added, and the agarose was solidified at room temperature for 1 h. 1 ml of the medium was placed on the agarose, and incubated at 27° C. for 4 days. When formation of plaques was confirmed, 0.01% Neutral Red in PBS was dropped on the agarose gel. The plate was incubated at 27° C. overnight, and it was confirmed that polyhedra were not formed in the plaques in colorless parts. Each of the plaque was sucked with a Pasteur pipette, and was suspended in 500 µl of the medium, and sonicated to break the agarose gel. The gel was sedimented by centrifugation, and the supernatant was diluted for further plaque cloning. The same step was repeated another two times. A recombinant baculovirus was obtained by carrying out the plaque cloning three times.

(7) Expression of Recombinant Protein in Insect Cell

Sf21AE cells were infected with the recombinant baculovirus at a multiplicity of infection (m.o.i.) of about 10, and the culture supernatant was recovered after 4 days. Culture supernatant which was infected with Autographa californica Nuclear Polyhedrosis Virus (AcNPV) was prepared similarly as the negative control.

(8) Bioassay

The biological activity of the feline G-CSF was assayed using mouse myeloblastoid cells NFS-60 whose growth is promoted by a mouse G-CSF. Feline cells are not used in this assay system, but it is popular to assay biological activity using a heterologous assay system in case that a low species-specificity of the objective cytokine is known, for example, interleukin-4 (Howard et al., 1982, J. Exp. Med., 155, 914), interleukin-7 (Conlon et al., 1989, Blood, 74, 1368). Human G-CSF were also assayed with mouse NFS-60 cells. NFS-60 cells were usually cultured using RPM1640 medium (Nissui Pharmaceutical) which was supplemented with 10% FBS and recombinant mouse interleukin-3 (mIL-3, Pepro Tech EC).

Bioassay was carried out using a Celltiter96 AQueous™ kit (Promega) as follows: NFS-60 cells were collected by centrifugation, rinsed twice with an 'mIL-3'-free medium, and adjusted to have a cell density of 2×10⁵/ml. 100 µl of the obtained suspension and 10 µl of recombinant human G-CSF (Gibco BRL) or serially diluted samples from the culture supernatant which was obtained in (6) were placed in each well of a 96-well plate, and were incubated for 24 h. The assay was carried out in duplicate per one dilution. After incubation, 20 µl of the reagent (Promega) for the assay was added to each well, incubated for additional 2 h, and an absorbance of each well was measured at 490 nm using an ELISA microplate reader. The more densely the cells grew, the higher the absorbance becomes.

The absorbance at 490 nm was low when the culture supernatant of AcNPV-infected cells was added, indicating that the cell proliferation was not promoted. In contrast, a high absorbance was obtained when the culture supernatant of the recombinant baculovirus-infected cells was added (see Table 3 below). The culture supernatant had the activity of the G-CSF. In addition, the cell proliferation-promoting activity became lower in accordance with the dilution, i.e., the activity was dose-dependent. Therefore, it was confirmed that the product of the gene has the G-CSF activity.

TABLE 3

| Dilution | AcNPV | Recombinant baculovirus | (pg/ml) | Recombinant human G-CSF |
| --- | --- | --- | --- | --- |
| 10⁷ | 0.019 | 0.238 | 0.1 | 0.030 |
| 10⁶ | 0.025 | 0.479 | 1 | 0.038 |
| 10⁵ | 0.029 | 0.690 | 10 | 0.072 |
| 10⁴ | 0.032 | 0.791 | 100 | 0.325 |
| 10³ | 0.037 | 0.805 | 1,000 | 0.786 |

Industrial Applicability

According to claim 1 of the present invention, a protein which has a G-CSF activity can be obtained. According to claims 5 and 6, pharmaceutical compositions and medicines which can be used for treating feline neutropenia can be provided.

According to claim 2 of the present invention, a gene which codes for the feline G-CSF protein can be obtained. According to claims 3, 4, and 7 of the present invention, a feline G-CSF protein can be produced in a large amount, and a medicine for neutropenia in cats can be inexpensively provided by expressing the gene by the genetic engineering techniques.

According to claims 8 and 9 of the present invention, an antibody can be obtained which is specific to a feline G-CSF protein, and a neutrophile-producing ability of a cat can be diagnosed using the same.

What is claimed is:

1. An isolated protein comprising an amino acid sequence set forth in SEQ ID NO. 2.

2. A pharmaceutical composition comprising the isolated protein of claim 1.

3. A method for producing a protein by culturing the host of claim 2 and collecting the protein.

4. An isolated polynucleotide which codes for a protein having an amino acid sequence as set forth in SEQ ID NO. 2.

5. A recombinant expression vector comprising the isolated polynucleotide of claim 4.

6. An isolated host transformed by the expression vector of claim 5.

* * * * *

SEQUENCE LISTING

<160> NUMBER OF SEQ ID NOS: 30

<210> SEQ ID NO 1
<211> LENGTH: 588

```
<212> TYPE: DNA
<213> ORGANISM: FERIDAE FELIS CATUS
<220> FEATURE:
<221> NAME/KEY: CDS
<222> LOCATION: (1)..(585)
<223> OTHER INFORMATION:
<220> FEATURE:
<221> NAME/KEY: mat_peptide
<222> LOCATION: (64)..()
<223> OTHER INFORMATION:
<220> FEATURE:
<221> NAME/KEY: variation
<222> LOCATION: (174)..(174)
<223> OTHER INFORMATION: /REPLACE = "T"
<220> FEATURE:
<221> NAME/KEY: sig_peptide
<222> LOCATION: (1)..(63)
<223> OTHER INFORMATION:

<400> SEQUENCE: 1 atg aag ctg acc gcc ctg cag ctg ctg ctg tgg cac agc gca ctc tgg      48
Met Lys Leu Thr Ala Leu Gln Leu Leu Leu Trp His Ser Ala Leu Trp
    -20             -15                 -10 atg gtg caa gaa gcc acc ccc ttg ggc cct acc agc tcc ctg ccc cag      96
Met Val Gln Glu Ala Thr Pro Leu Gly Pro Thr Ser Ser Leu Pro Gln
 -5              -1   1               5                  10 agc ttc ctg ctc aag tgc tta gaa caa gtg agg aag gtc cag gct gat     144
Ser Phe Leu Leu Lys Cys Leu Glu Gln Val Arg Lys Val Gln Ala Asp
             15                  20                  25 ggc aca gcg ctg cag gag agg ctg tgc gcc gcc cac aag ctg tgc cac     192
Gly Thr Ala Leu Gln Glu Arg Leu Cys Ala Ala His Lys Leu Cys His
         30                  35                  40 cct gag gag ctg gtg ctg ctt ggg cac gct ctg ggc atc ccc cag gct     240
Pro Glu Glu Leu Val Leu Leu Gly His Ala Leu Gly Ile Pro Gln Ala
     45                  50                  55 ccc ctg agc agc tgc tcc agc cag gcc ctg cag ctg acg ggc tgc ctg     288
Pro Leu Ser Ser Cys Ser Ser Gln Ala Leu Gln Leu Thr Gly Cys Leu
 60                  65                  70                  75 cgt caa ctc cac agt ggc ctc ttc ctc tac cag ggc ctc ctg cag gcc     336
Arg Gln Leu His Ser Gly Leu Phe Leu Tyr Gln Gly Leu Leu Gln Ala
                 80                  85                  90 ctg gca ggg ata tcc ccc gag tta gcc ccc acc ctg gac atg ctg cag     384
Leu Ala Gly Ile Ser Pro Glu Leu Ala Pro Thr Leu Asp Met Leu Gln
             95                 100                 105 ctg gac atc acc gac ttt gct atc aac atc tgg cag cag atg gaa gac     432
Leu Asp Ile Thr Asp Phe Ala Ile Asn Ile Trp Gln Gln Met Glu Asp
        110                 115                 120 gtg ggg atg gcc cct gca gtg ccg ccc acc cag ggc acc atg cca acc     480
Val Gly Met Ala Pro Ala Val Pro Pro Thr Gln Gly Thr Met Pro Thr
    125                 130                 135 ttc acc tcg gcc ttc cag cgc cgg gca gga ggc acc ctg gtt gcc tcc     528
Phe Thr Ser Ala Phe Gln Arg Arg Ala Gly Gly Thr Leu Val Ala Ser
140                 145                 150                 155 aac ctg cag agc ttc ctg gag gtg gca tac cgt gct ctg cgc cac ttc     576
Asn Leu Gln Ser Phe Leu Glu Val Ala Tyr Arg Ala Leu Arg His Phe
                160                 165                 170 aac aag ccc tga                                                     588
Asn Lys Pro <210> SEQ ID NO 2
<211> LENGTH: 195
<212> TYPE: PRT
<213> ORGANISM: FERIDAE FELIS CATUS

<400> SEQUENCE: 2
```

```
Met Lys Leu Thr Ala Leu Gln Leu Leu Trp His Ser Ala Leu Trp
    -20             -15              -10
Met Val Gln Glu Ala Thr Pro Leu Gly Pro Thr Ser Ser Leu Pro Gln
 -5          -1   1              5                       10
Ser Phe Leu Leu Lys Cys Leu Glu Gln Val Arg Lys Val Gln Ala Asp
             15              20              25
Gly Thr Ala Leu Gln Glu Arg Leu Cys Ala Ala His Lys Leu Cys His
             30              35              40
Pro Glu Glu Leu Val Leu Leu Gly His Ala Leu Gly Ile Pro Gln Ala
             45              50              55
Pro Leu Ser Ser Cys Ser Ser Gln Ala Leu Gln Leu Thr Gly Cys Leu
 60              65              70              75
Arg Gln Leu His Ser Gly Leu Phe Leu Tyr Gln Gly Leu Leu Gln Ala
                 80              85              90
Leu Ala Gly Ile Ser Pro Glu Leu Ala Pro Thr Leu Asp Met Leu Gln
                 95             100             105
Leu Asp Ile Thr Asp Phe Ala Ile Asn Ile Trp Gln Gln Met Glu Asp
            110             115             120
Val Gly Met Ala Pro Ala Val Pro Pro Thr Gln Gly Thr Met Pro Thr
        125             130             135
Phe Thr Ser Ala Phe Gln Arg Arg Ala Gly Gly Thr Leu Val Ala Ser
140             145             150                         155
Asn Leu Gln Ser Phe Leu Glu Val Ala Tyr Arg Ala Leu Arg His Phe
            160             165             170
Asn Lys Pro

<210> SEQ ID NO 3
<211> LENGTH: 29
<212> TYPE: DNA
<213> ORGANISM: Artificial Sequence
<220> FEATURE:
<223> OTHER INFORMATION: HYPOTHETICAL SEQUENCE

<400> SEQUENCE: 3
cgccaagctt cagagcttcc tgctcaagt                                    29

<210> SEQ ID NO 4
<211> LENGTH: 26
<212> TYPE: DNA
<213> ORGANISM: Artificial Sequence
<220> FEATURE:
<223> OTHER INFORMATION: HYPOTHETICAL SEQUENCE

<400> SEQUENCE: 4
cggaattcct gctgccagat gttgat                                       26

<210> SEQ ID NO 5
<211> LENGTH: 20
<212> TYPE: DNA
<213> ORGANISM: Artificial Sequence
<220> FEATURE:
<223> OTHER INFORMATION: HYPOTHETICAL SEQUENCE

<400> SEQUENCE: 5
ctccaccacc cctctccagc                                              20

<210> SEQ ID NO 6
<211> LENGTH: 33
<212> TYPE: DNA
```

<213> ORGANISM: Artificial Sequence
<220> FEATURE:
<223> OTHER INFORMATION: HYPOTHETICAL SEQUENCE

<400> SEQUENCE: 6
cgcggatcct gcagcgcagt gccatcagcc tgg                                    33

<210> SEQ ID NO 7
<211> LENGTH: 20
<212> TYPE: DNA
<213> ORGANISM: Artificial Sequence
<220> FEATURE:
<223> OTHER INFORMATION: HYPOTHETICAL SEQUENCE

<400> SEQUENCE: 7
ggcctcctgc aggccctggc                                                   20

<210> SEQ ID NO 8
<211> LENGTH: 34
<212> TYPE: DNA
<213> ORGANISM: Artificial Sequence
<220> FEATURE:
<223> OTHER INFORMATION: HYPOTHETICAL SEQUENCE

<400> SEQUENCE: 8
cgcggatccg ctggacatca ccgactttgc tatc                                   34

<210> SEQ ID NO 9
<211> LENGTH: 44
<212> TYPE: DNA
<213> ORGANISM: Artificial Sequence
<220> FEATURE:
<223> OTHER INFORMATION: HYPOTHETICAL SEQUENCE

<400> SEQUENCE: 9
gtacatattg tcgttagaac gcggaattcg actcactata ggga                        44

<210> SEQ ID NO 10
<211> LENGTH: 48
<212> TYPE: DNA
<213> ORGANISM: Artificial Sequence
<220> FEATURE:
<223> OTHER INFORMATION: HYPOTHETICAL SEQUENCE
<220> FEATURE:
<221> NAME/KEY: misc_feature
<223> OTHER INFORMATION: PRESENTED 3' TO 5' ORIENTATION

<400> SEQUENCE: 10
catgtataac agcaatcttg cgccttaagc tgagtgatat ccctctag                    48

<210> SEQ ID NO 11
<211> LENGTH: 50
<212> TYPE: DNA
<213> ORGANISM: Artificial Sequence
<220> FEATURE:
<223> OTHER INFORMATION: HYPOTHETICAL SEQUENCE

<400> SEQUENCE: 11
gtacatattg tcgttagaac gcggaattcg actcactata gggagacatg                  50

<210> SEQ ID NO 12
<211> LENGTH: 46
<212> TYPE: DNA
<213> ORGANISM: Artificial Sequence
<220> FEATURE:
<223> OTHER INFORMATION: HYPOTHETICAL SEQUENCE
<220> FEATURE:

```
<221> NAME/KEY: misc_feature
<223> OTHER INFORMATION: PRESENTED 3' TO 5' ORIENTATION

<400> SEQUENCE: 12
catgtataac agcaatcttg cgccttaagc tgagtgatat ccctct          46

<210> SEQ ID NO 13
<211> LENGTH: 44
<212> TYPE: DNA
<213> ORGANISM: Artificial Sequence
<220> FEATURE:
<223> OTHER INFORMATION: HYPOTHETICAL SEQUENCE

<400> SEQUENCE: 13
gtacatattg tcgttagaac gcggaattcg actcactata ggga            44

<210> SEQ ID NO 14
<211> LENGTH: 48
<212> TYPE: DNA
<213> ORGANISM: Artificial Sequence
<220> FEATURE:
<223> OTHER INFORMATION: HYPOTHETICAL SEQUENCE
<220> FEATURE:
<221> NAME/KEY: misc_feature
<223> OTHER INFORMATION: PRESENTED 3' TO 5' ORIENTATION

<400> SEQUENCE: 14
catgtataac agcaatcttg cgccttaagc tgagtgatat ccctttaa        48

<210> SEQ ID NO 15
<211> LENGTH: 35
<212> TYPE: DNA
<213> ORGANISM: Artificial Sequence
<220> FEATURE:
<223> OTHER INFORMATION: HYPOTHETICAL SEQUENCE

<400> SEQUENCE: 15
gtacatattg tcgttagaac gcgtaatacg actca                      35

<210> SEQ ID NO 16
<211> LENGTH: 35
<212> TYPE: DNA
<213> ORGANISM: Artificial Sequence
<220> FEATURE:
<223> OTHER INFORMATION: HYPOTHETICAL SEQUENCE

<400> SEQUENCE: 16
cgttagaacg cggaattcga ctcactatag gaga                       35

<210> SEQ ID NO 17
<211> LENGTH: 20
<212> TYPE: DNA
<213> ORGANISM: Artificial Sequence
<220> FEATURE:
<223> OTHER INFORMATION: HYPOTHETICAL SEQUENCE

<400> SEQUENCE: 17
ttccagcgcc gggcaggagg                                       20

<210> SEQ ID NO 18
<211> LENGTH: 28
<212> TYPE: DNA
<213> ORGANISM: Artificial Sequence
<220> FEATURE:
<223> OTHER INFORMATION: HYPOTHETICAL SEQUENCE

<400> SEQUENCE: 18
```

```
cgcggatccc tgcagagctt cctggagg                                              28

<210> SEQ ID NO 19
<211> LENGTH: 28
<212> TYPE: DNA
<213> ORGANISM: Artificial Sequence
<220> FEATURE:
<223> OTHER INFORMATION: HYPOTHETICAL SEQUENCE

<400> SEQUENCE: 19
cgcggatcca tgaagctgac cgccctgc                                              28

<210> SEQ ID NO 20
<211> LENGTH: 28
<212> TYPE: DNA
<213> ORGANISM: Artificial Sequence
<220> FEATURE:
<223> OTHER INFORMATION: HYPOTHETICAL SEQUENCE

<400> SEQUENCE: 20
cgcggatcct tttcagggct tggtgaag                                              28

<210> SEQ ID NO 21
<211> LENGTH: 20
<212> TYPE: DNA
<213> ORGANISM: Artificial Sequence
<220> FEATURE:
<223> OTHER INFORMATION: HYPOTHETICAL SEQUENCE

<400> SEQUENCE: 21
aaatacactc gtgagggagg                                                       20

<210> SEQ ID NO 22
<211> LENGTH: 18
<212> TYPE: DNA
<213> ORGANISM: Artificial Sequence
<220> FEATURE:
<223> OTHER INFORMATION: HYPOTHETICAL SEQUENCE

<400> SEQUENCE: 22
cagctgcagg gcctggct                                                         18

<210> SEQ ID NO 23
<211> LENGTH: 20
<212> TYPE: DNA
<213> ORGANISM: Artificial Sequence
<220> FEATURE:
<223> OTHER INFORMATION: HYPOTHETICAL SEQUENCE

<400> SEQUENCE: 23
ggaattccag gcctccatgg                                                       20

<210> SEQ ID NO 24
<211> LENGTH: 27
<212> TYPE: DNA
<213> ORGANISM: Artificial Sequence
<220> FEATURE:
<223> OTHER INFORMATION: HYPOTHETICAL SEQUENCE

<400> SEQUENCE: 24
ggaattcgat aaatacactc gtgaggg                                               27

<210> SEQ ID NO 25
<211> LENGTH: 19
<212> TYPE: DNA
```

```
<213> ORGANISM: Artificial Sequence
<220> FEATURE:
<223> OTHER INFORMATION: HYPOTHETICAL SEQUENCE

<400> SEQUENCE: 25
cagagcttcc tgctcaagt                                                19

<210> SEQ ID NO 26
<211> LENGTH: 19
<212> TYPE: DNA
<213> ORGANISM: Artificial Sequence
<220> FEATURE:
<223> OTHER INFORMATION: HYPOTHETICAL SEQUENCE

<400> SEQUENCE: 26
cctgcaggag gccctggta                                                19

<210> SEQ ID NO 27
<211> LENGTH: 20
<212> TYPE: DNA
<213> ORGANISM: Artificial Sequence
<220> FEATURE:
<223> OTHER INFORMATION: HYPOTHETICAL SEQUENCE

<400> SEQUENCE: 27
atgggctgcc tgcgtcaact                                               20

<210> SEQ ID NO 28
<211> LENGTH: 207
<212> TYPE: PRT
<213> ORGANISM: Homo sapiens

<400> SEQUENCE: 28

Met Ala Gly Pro Ala Thr Gln Ser Pro Met Lys Leu Met Ala Leu Gln
1               5                   10                  15

Leu Leu Leu Trp His Ser Ala Leu Trp Thr Val Gln Glu Ala Thr Pro
            20                  25                  30

Leu Gly Pro Ala Ser Ser Leu Pro Gln Ser Phe Leu Leu Lys Cys Leu
        35                  40                  45

Glu Gln Val Arg Lys Ile Gln Gly Asp Gly Ala Ala Leu Gln Glu Lys
    50                  55                  60

Leu Val Ser Glu Cys Ala Thr Tyr Lys Leu Cys His Pro Glu Glu Leu
65                  70                  75                  80

Val Leu Leu Gly His Ser Leu Gly Ile Pro Trp Ala Pro Leu Ser Ser
                85                  90                  95

Cys Pro Ser Gln Ala Leu Gln Leu Ala Gly Cys Leu Ser Gln Leu His
            100                 105                 110

Ser Gly Leu Phe Leu Tyr Gln Gly Leu Leu Gln Ala Leu Glu Gly Ile
        115                 120                 125

Ser Pro Glu Leu Gly Pro Thr Leu Asp Thr Leu Gln Leu Asp Val Ala
    130                 135                 140

Asp Phe Ala Thr Thr Ile Trp Gln Gln Met Glu Glu Leu Gly Met Ala
145                 150                 155                 160

Pro Ala Leu Gln Pro Thr Gln Gly Ala Met Pro Ala Phe Ala Ser Ala
                165                 170                 175

Phe Gln Arg Arg Ala Gly Gly Val Leu Val Ala Ser His Leu Gln Ser
            180                 185                 190

Phe Leu Glu Val Ser Tyr Arg Val Leu Arg His Leu Ala Gln Pro
        195                 200                 205
```

<210> SEQ ID NO 29
<211> LENGTH: 208
<212> TYPE: PRT
<213> ORGANISM: MOUSE

<400> SEQUENCE: 29

```
Met Ala Gln Leu Ser Ala Gln Arg Arg Met Lys Leu Met Ala Leu Gln
1               5                   10                  15

Leu Leu Leu Trp Gln Ser Ala Leu Trp Ser Gly Arg Glu Ala Val Pro
            20                  25                  30

Leu Val Thr Val Ser Ala Leu Pro Pro Ser Leu Pro Leu Pro Arg Ser
        35                  40                  45

Phe Leu Leu Lys Ser Leu Glu Gln Val Arg Lys Ile Gln Ala Ser Gly
    50                  55                  60

Ser Val Leu Leu Glu Glu Leu Cys Ala Thr Tyr Lys Leu Cys His Pro
65                  70                  75                  80

Glu Glu Leu Val Leu Leu Gly His Ser Leu Gly Ile Pro Lys Ala Ser
                85                  90                  95

Leu Ser Gly Cys Ser Ser Gln Ala Leu Gln Gln Thr Gln Cys Leu Ser
            100                 105                 110

Gln Leu His Ser Gly Leu Cys Leu Tyr Gln Gly Leu Leu Gln Ala Leu
        115                 120                 125

Ser Gly Ile Ser Pro Ala Leu Ala Pro Thr Leu Asp Leu Leu Gln Leu
    130                 135                 140

Asp Val Ala Asn Phe Ala Thr Thr Ile Trp Gln Gln Met Glu Asn Leu
145                 150                 155                 160

Gly Val Ala Pro Thr Val Gln Pro Thr Gln Ser Ala Met Pro Ala Phe
                165                 170                 175

Thr Ser Ala Phe Gln Arg Arg Ala Gly Gly Val Leu Ala Ile Ser Tyr
            180                 185                 190

Leu Gln Gly Phe Leu Glu Thr Ala Arg Leu Ala Leu His His Leu Ala
        195                 200                 205
```

<210> SEQ ID NO 30
<211> LENGTH: 195
<212> TYPE: PRT
<213> ORGANISM: FERIDAE FELIS CATUS

<400> SEQUENCE: 30

```
Met Lys Leu Thr Ala Leu Gln Leu Leu Trp His Ser Ala Leu Trp
1               5                   10                  15

Met Val Gln Glu Ala Thr Pro Leu Gly Pro Thr Ser Ser Leu Pro Gln
            20                  25                  30

Ser Phe Leu Leu Lys Cys Leu Glu Gln Val Arg Lys Val Gln Ala Asp
        35                  40                  45

Gly Thr Ala Leu Gln Glu Arg Leu Cys Ala Ala His Lys Leu Cys His
    50                  55                  60

Pro Glu Glu Leu Val Leu Leu Gly His Ala Leu Gly Ile Pro Gln Ala
65                  70                  75                  80

Pro Leu Ser Ser Cys Ser Ser Gln Ala Leu Gln Leu Thr Gly Cys Leu
                85                  90                  95

Arg Gln Leu His Ser Gly Leu Phe Leu Tyr Gln Gly Leu Leu Gln Ala
            100                 105                 110

Leu Ala Gly Ile Ser Pro Glu Leu Ala Pro Thr Leu Asp Met Leu Gln
        115                 120                 125
```

```
Leu Asp Ile Thr Asp Phe Ala Ile Asn Ile Trp Gln Gln Met Glu Asp
    130                 135                 140

Val Gly Met Ala Pro Ala Val Pro Pro Thr Gln Gly Thr Met Pro Thr
145                 150                 155                 160

Phe Thr Ser Ala Phe Gln Arg Arg Ala Gly Gly Thr Leu Val Ala Ser
                165                 170                 175

Asn Leu Gln Ser Phe Leu Glu Val Ala Tyr Arg Ala Leu Arg His Phe
            180                 185                 190

Thr Lys Pro
        195
```